United States Patent
He

(10) Patent No.: US 11,707,248 B2
(45) Date of Patent: Jul. 25, 2023

(54) AUTOMATIC EXPOSURE CONTROL METHOD FOR X-RAY IMAGING, STORAGE MEDIUM AND MEDICAL DEVICE

(71) Applicant: Siemens Healthcare GmbH, Erlangen (DE)

(72) Inventor: Wei He, Shanghai (CN)

(73) Assignee: Siemens Healthcare GmbH, Erlangen (DE)

(*) Notice: Subject to any disclaimer, the term of this patent is extended or adjusted under 35 U.S.C. 154(b) by 228 days.

(21) Appl. No.: 17/298,413

(22) PCT Filed: Nov. 22, 2019

(86) PCT No.: PCT/EP2019/082178
§ 371 (c)(1),
(2) Date: May 28, 2021

(87) PCT Pub. No.: WO2020/109149
PCT Pub. Date: Jun. 4, 2020

(65) Prior Publication Data
US 2022/0117571 A1 Apr. 21, 2022

(30) Foreign Application Priority Data
Nov. 28, 2018 (CN) .......................... 201811429851.2

(51) Int. Cl.
*A61B 6/00* (2006.01)
(52) U.S. Cl.
CPC .............. *A61B 6/542* (2013.01); *A61B 6/469* (2013.01); *A61B 6/488* (2013.01)

(58) Field of Classification Search
CPC .......... A61B 6/542; A61B 6/469; A61B 6/488
See application file for complete search history.

(56) References Cited

U.S. PATENT DOCUMENTS

| 10,285,661 B2 | 5/2019 | Morf et al. | |
|---|---|---|---|
| 2002/0085672 A1* | 7/2002 | Ganin | H05G 1/30 378/108 |

(Continued)

FOREIGN PATENT DOCUMENTS

| CN | 101846640 A | 9/2010 |
|---|---|---|
| CN | 102809869 A | 12/2012 |

(Continued)

OTHER PUBLICATIONS

Patent Cooperation Treaty International Search Report dated Mar. 19, 2020, Application No. PCT/EP2019/082178.

*Primary Examiner* — Courtney D Thomas
(74) *Attorney, Agent, or Firm* — Banner & Witcoff Ltd.

(57) ABSTRACT

In an automatic exposure control method for X-ray imaging, a visible light image of a subject under test is acquired, an initial region of interest (ROI) is defined on the visible light image, the subject under test is pre-exposed with a set pre-exposure dose to obtain a first image, an ROI on the first image is defined based on the initial ROI, a reference pixel value is defined based on the ROI, and a main exposure dose for an actual exposure is calculated according to the reference pixel value. With the imaging quality guaranteed, a physical automatic exposure control (AEC) chamber may be omitted, and the number, positions and sizes of ROIs can be adjusted according to the actual requirements.

17 Claims, 4 Drawing Sheets

(56) References Cited

U.S. PATENT DOCUMENTS

2005/0242269 A1  11/2005  Hayashi et al.
2010/0177947 A1   7/2010  Hayashi et al.
2014/0348299 A1  11/2014  Sung et al.

FOREIGN PATENT DOCUMENTS

| CN | 104146724 A | 11/2014 |
| CN | 106550527 A | 3/2017 |
| CN | 109745060 A | 5/2019 |
| JP | 2017220403 A | 12/2017 |
| WO | 2018210175 A1 | 11/2018 |

* cited by examiner

AUTOMATIC EXPOSURE CONTROL METHOD FOR X-RAY IMAGING, STORAGE MEDIUM AND MEDICAL DEVICE

CROSS REFERENCE TO RELATED APPLICATIONS

This patent application is a National Stage Application of International Patent Application No. PCT/EP2019/082178, filed Nov. 22, 2019, which claims priority to Chinese Patent Application No. 201811429851.2, filed Nov. 28, 2018. Each of these applications is incorporated herein by reference in its entirety.

BACKGROUND

Technical Field

The present disclosure relates to the technical field of medical apparatuses and instruments, and in particular relates to an automatic exposure control method for X-ray imaging, a computer storage medium and an X-ray medical device.

Background Art

Automatic exposure control (AEC) chambers are usually put before the detectors of an X-ray medical device to calculate the pre-estimated dose of the region-of-interest (ROI) to be checked each time. More AEC chambers will increase not only the measurement accuracy, but also the cost.

A plurality of solutions in which no AEC chambers are used have been proposed, and some of these solutions utilize some pixels or pixel groups to play the role of AEC chambers. These pixels or pixel groups are controlled and read one by one. This increases the complexity of detectors and thus increases the cost of detectors. For example, the Chinese patent application (publication No.: CN106550527A) relates to a method of acquiring an X-ray image, and AEC pixels are arranged above a detector array in the method.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
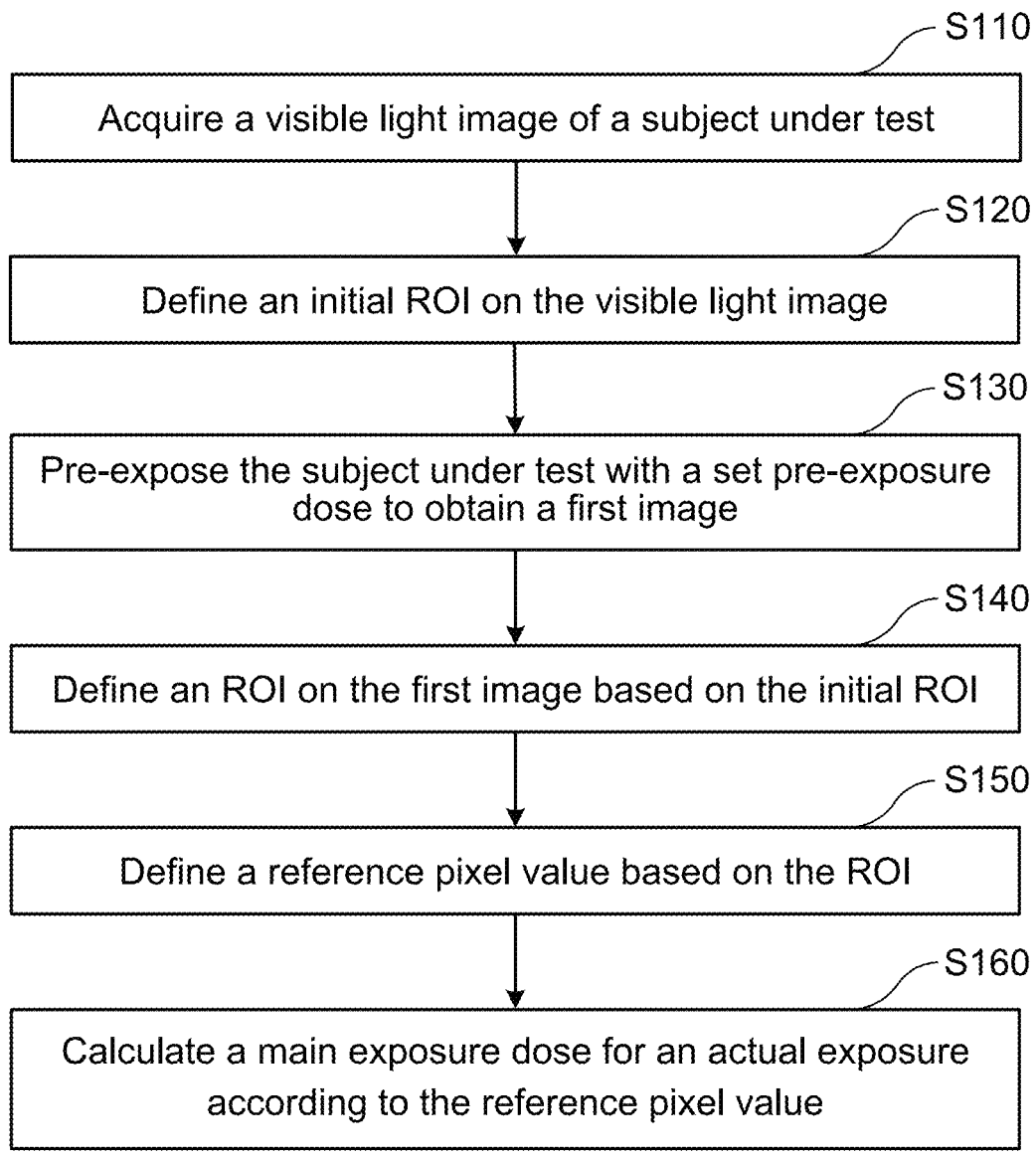
FIG. 1 is a schematic flow chart of the automatic exposure control method for X-ray imaging according to an exemplary embodiment of the present disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

In this document, "schematic" means "acting as an instance, example, or illustration", and any "schematic" illustration or embodiment described in this document should not be interpreted as a more preferred or advantageous technical solution.

For the simplicity of the drawings, only the parts related to the present disclosure are shown for a schematic purpose and they do not represent actual structures of a product. In addition, only one of the components which have the same structure or function is depicted or marked for a schematic purpose in some drawings so that the drawings are simplified to help to understand.

In this document, "one" not only represents "only one", but also may represent "more than one". "Pre-exposure" in this document means exposure with a exposure dose much lower than a normal exposure dose, and the "first image" obtained from a pre-exposure, also known as "pre-exposure image", is actually an image obtained from an exposure with a low exposure dose. "Main exposure" means actual exposure or normal exposure for X-ray detection, and the image obtained from "main exposure" satisfies the image quality requirements for medical diagnoses and subsequent processing for the subject under test.

In this document, if the X-ray device registration is completed, a correspondence exists between "the corresponding point of the center of an X-ray beam on the visible light image" and the central point of the detector of the X-ray medical device, and a correspondence exists between "the corresponding point of the center of an X-ray beam on the visible light image" and the center of the visible light image. In practice, a pixel point coordinate correspondence exists between the visible light image and the pre-exposure image obtained from exposure with a low exposure dose (first image), and if the X-ray device registration is completed, a correspondence exists between the corresponding point of the center of an X-ray beam on the visible light image, the center of the visible light image and the center of the first image. The position of an ROI can defined according to the centers of the visible light image and the first image during image processing. This will be described in detail below in combination with the drawings.

Conventionally, complex image processing needs to be performed to obtain the exposure dose required for an actual exposure in the field of X-ray imaging. For example, complex image processing methods such as image edge extraction and image segmentation are adopted to process a "pre-exposure image" generated by a detector, and then an ROI is defined on the "pre-exposure image". For the imaging of complex tissues, the robustness of the methods such as pre-exposure image based edge extraction and segmentation is low, and incorrect processing will lead to an inaccurate dose calculation: too low a dose will cause a poor image quality and re-shooting is required; too high a dose will additionally increase the dose of a patient.

Advantageously, by adapting the conventional complex image processing method to allow the operator select an ROI, the image processing complexity can be greatly simplified and the operation speed can be improved.

An automatic exposure control method for X-ray imaging is provided in one aspect of the present disclosure, a computer storage medium is provided in another aspect, and an X-ray medical device is provided in a further aspect.

According to one embodiment, the automatic exposure control method for X-ray imaging comprises: acquiring a visible light image of a subject under test, defining an initial ROI on the visible light image, pre-exposing the subject under test with a set pre-exposure dose to obtain a first image, defining an ROI on the first image based on the initial ROI, defining a reference pixel value based on the ROI, and calculating a main exposure dose for an actual exposure according to the reference pixel value.

In an exemplary embodiment, defining an initial ROI on the visible light image comprises: displaying a preset selection box on the visible light image, and defining the at least one initial ROI by moving or adjusting the preset selection box on the visible light image.

In an exemplary embodiment, the preset selection box is a preset selection box which is set in a preset position on the visible light image and has a preset size, or the preset selection box is a preset selection box which is set in different positions according to the subject under test displayed on the visible light image and has different sizes.

In an exemplary embodiment, defining an initial ROI on the visible light image comprises: box-selecting an initial ROI on the visible light image.

In an exemplary embodiment, defining an ROI on the first image comprises the following steps: defining the distance from the center of the initial ROI to the corresponding point of the center of an X-ray beam on the visible light image, and defining the position of the ROI on the first image according to the distance.

According to one embodiment, program instructions are stored in the computer storage medium and the program instructions can be run to realize any above-mentioned method.

According to one embodiment, the X-ray medical device comprises: a shooting unit, used to collect a visible light image of a subject under test, an exposure unit, used to pre-expose the subject under test with a set pre-exposure dose to obtain a first image, and a controller, the controller being configured to: acquire a visible light image of the subject under test, define an initial ROI on the visible light image, define an ROI on the first image based on the initial ROI, define a reference pixel value based on the ROI, and calculate a main exposure dose for an actual exposure according to the reference pixel value.

In an exemplary embodiment, the controller is further configured to: display a preset selection box on the visible light image, and define the at least one initial ROI by moving or adjusting the preset selection box on the visible light image.

In an exemplary embodiment, the preset selection box is a preset selection box which is set in a preset position on the visible light image and has a preset size, or the preset selection box is a preset selection box which is set in different positions according to the subject under test displayed on the visible light image and has different sizes.

In an exemplary embodiment, the controller is further configured to: box-select an initial ROI on the visible light image.

In an exemplary embodiment, the controller is further configured to define an ROI by performing the following steps: defining the distance from the center of the initial ROI to the corresponding point of the center of an X-ray beam on the visible light image, and defining the position of the ROI on the first image according to the distance.

With the imaging quality guaranteed, the present disclosure can spare a physical automatic exposure control (AEC) chamber, and the number, positions and sizes of ROIs can be adjusted according to the actual requirements. The present disclosure is more flexible in patient positioning. In addition, the present disclosure simplifies operations and improves the image processing speed.

First, see FIG. 1. FIG. 1 is a schematic flow chart of the automatic exposure control method for X-ray imaging according to one embodiment of the present disclosure. In the embodiment shown in FIG. 1, the automatic exposure control method 100 for X-ray imaging comprises:

Step S110: Acquire a visible light image of a subject under test,

Step S120: Define an initial ROI on the visible light image,

Step S130: Pre-expose the subject under test with a set pre-exposure dose to obtain a first image, Step S140: Define an ROI on the first image based on the initial ROI, Step S150: Define a reference pixel value based on the ROI, and Step S160: Calculate a main exposure dose for an actual exposure according to the reference pixel value.

Figure 2A:
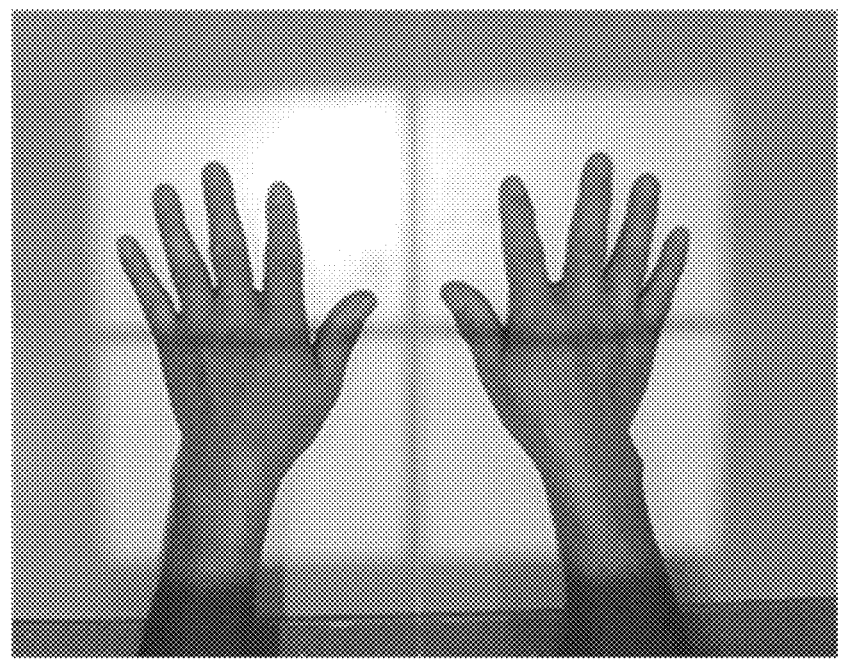
FIGS. 2A and 2B are schematic diagrams for visible light images according to exemplary embodiments of the present disclosure.
Figure 2B:
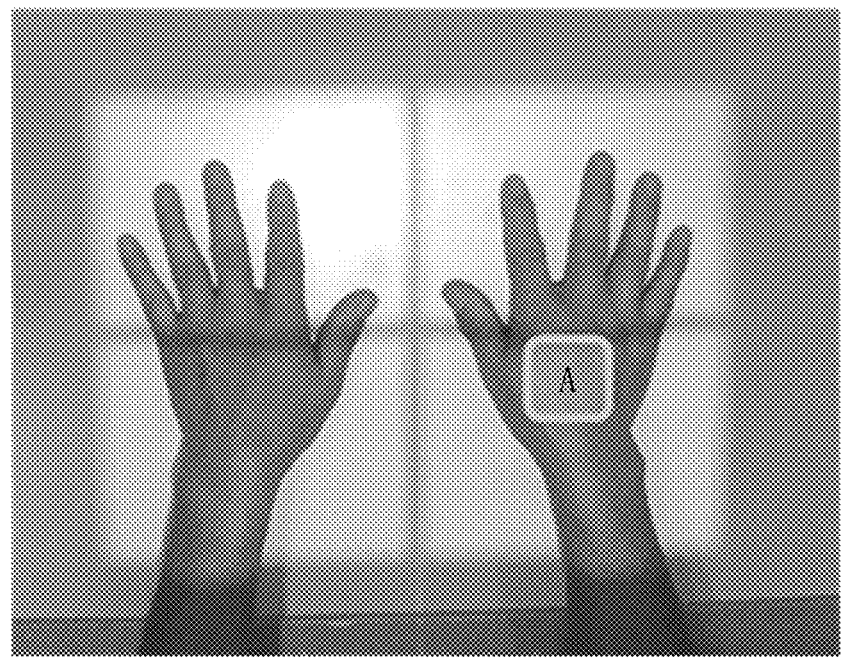

In Step S110, a visible light image of a subject under test (for example, an organ or body part) is acquired. As shown in FIG. 2A, the subject under test is hands, and the subject under test is not limited to hands in the present disclosure. In Step S120, an initial ROI, for example, region A shown in FIG. 2B, is defined on the visible light image. In the embodiments, the initial ROI can be defined in different ways. Those skilled in the art can select and set the position, shape, size and number of initial ROIs according to the requirements, and they are not restricted in the present disclosure. For example, a preset selection box (not shown) can be displayed on the visible light image shown in FIG. 2A, and the preset selection box can be a preset selection box which is set in a preset position on the visible light image and has a preset size, or a preset selection box which is set in different positions according to the subject under test on the visible light image and has different sizes. For example, a preset selection box can be a default selection box located in the middle or other positions of the visible light image shown in FIG. 2A, and the operator can define an initial ROI by moving or adjusting the preset selection box on the visible light image. Or, the preset selection box can be a different pre-estimated selection box provided according to the subject under test on the visible light image, and the preset selection box is provided for the operator to confirm or set the initial ROI. For example, the range of the subject under test on the visible light image is defined by use of the imaging processing method such as contour extraction or the target identification method such as machine learning, and in a proper position on the visible light image, a pre-estimated selection box with a proper size is provided as the above-mentioned preset selection box for subsequent operations. In other words, for different subjects under test, a pre-estimated selection box located in different positions on the visible light image and having different sizes can be provided as a preset selection box. Alternatively, no preset selection box is provided and the operator arbitrarily box-selects an initial ROI on the visible light image.

Figure 3A:
FIGS. 3A and 3B are schematic diagrams for the first image obtained from pre-exposure according to exemplary embodiments of the present disclosure.

In Step S130, the subject under test is pre-exposed with a set pre-exposure dose to obtain a first image, as shown in FIG. 3A. For a digital detector, the responses of signals to radiation are generally linear in an unsaturated region. Wherein, the first image (namely, the image obtained from an exposure with a low dose) is obtained from an exposure with a very low pre-exposure dose and the pre-exposure dose can be set according to the selection result of the organ program (OPG). Generally speaking, the thicker the subject under test is, the larger the pre-exposure dose is. In practice, the main exposure dose can be pre-stored to define the pre-exposure dose, and the pre-stored main exposure dose is an empirical dose satisfying the imaging requirement of the subject under test. Those skilled in the art can use other methods than the methods exemplified above to select and set a pre-exposure dose according to the actual application requirements.

Figure 3B:
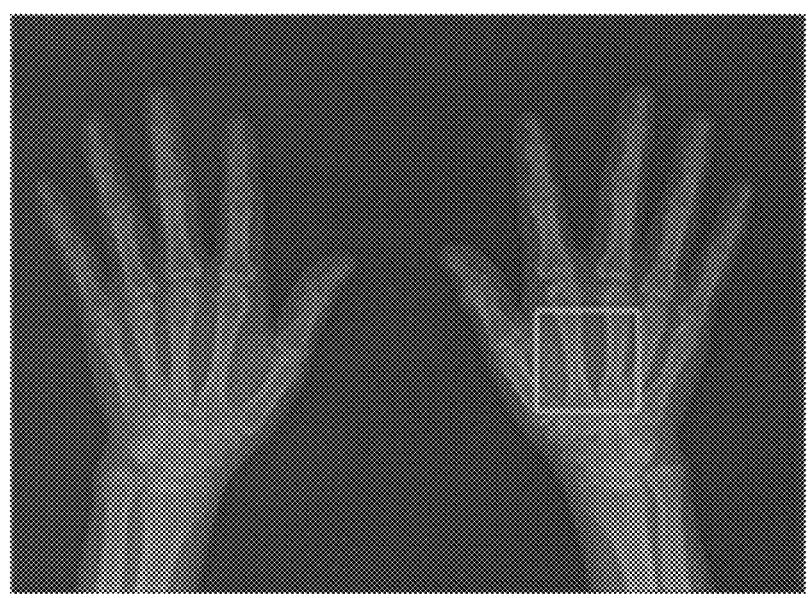

Then, in Step S140, an ROI is defined on the first image based on the initial ROI. In the embodiments, the distance from the center of the initial ROI A to the corresponding point of the center of an X-ray beam on the visible light image can be defined, and the position of the ROI on the first image shown in FIG. 3A can be defined according to the distance (as shown in FIG. 3B). As previously described, if the X-ray device registration is completed, the center of the visible light image can be viewed as a reference point, the distance from the center of the initial ROI A to the reference point can be defined. In addition, since a pixel point coordinate correspondence exists between the visible light image and the first image, the ROI corresponding to the initial ROI A, namely, the region shown in FIG. 3B, can be found on the first image based on the distance, with the center of the first image as a reference. In variant embodiments, the operator can adjust the size of the ROI according to the specific conditions and examination requirements of the subject under test (for example, organ) displayed on the visible light image.

Then, Steps S150 and S160 are performed. In Step S150, a reference pixel value is defined based on the ROI, and in Step S160, the main exposure dose for an actual exposure is calculated according to the reference pixel value. For how to perform these two steps, a schematic description is given below.

In Step S150, a reference pixel value is defined based on the ROI. Particularly, the reference pixel value can be defined, for example, by calculating the average pixel value of the ROI. If the operator selects a plurality of regions as ROIs, then the reference pixel value can be defined by calculating the average pixel value of the selected regions, or the reference pixel value can be defined by assigning a weight to the selected regions and then weighting the pixel values of the selected regions.

Alternatively, in order to improve the image processing speed and lower the operation time, the first image can be partially read based on the ROI. For example, only the partial image containing line pixels and column pixels of the ROI is read and processed. In addition, those skilled in the art can select the full resolution to read the first image or a low resolution to read the first image according to the actual requirements, and in this case, the first image can be read in a specific image reading mode (for example, binning).

Then, in Step S160; a main exposure dose for an actual exposure is calculated according to the reference pixel value. Thus, the dose required for the actual exposure (main exposure) can be calculated for each examination. In an exemplary embodiment, the main exposure dose Mr can be calculated according to the following formula:

$$Mr = Mp * \frac{G_{target}}{G_{ROI}} * D\%$$

Wherein, Mp is the set pre-exposure dose, $G_{ROI}$ is the average pixel value (namely, reference pixel value) of an ROI, $G_{target}$ is the preset average pixel value satisfying the imaging requirements, and D % wherein, Mp is the set pre-exposure dose, $G_{ROI}$ is the average pixel value (namely, reference pixel value) of an ROI, $G_{target}$ is the preset average pixel value satisfying the imaging requirements, and D % is a preset dose factor, which represents the dose level. Those skilled in the art can preset or adjust the above-mentioned $G_{target}$ D % according to the actual requirements.

Figure 4:
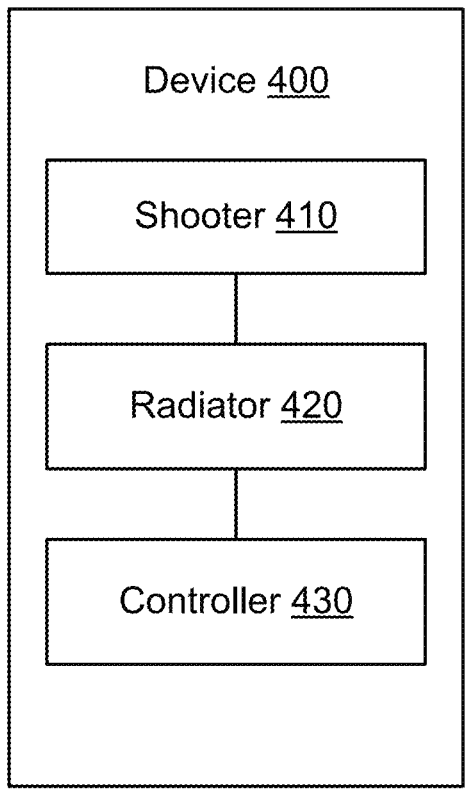
FIG. 4 is a schematic block diagram for the X-ray medical device according to an exemplary embodiment of the present disclosure.

The present disclosure further provides an X-ray medical device, which, for example, can be used to realize the above-mentioned automatic exposure control method for X-ray imaging. See FIG. 4. FIG. 4 is a schematic block diagram for the X-ray medical device according to one embodiment of the present disclosure. As shown in FIG. 4, the X-ray medical device 400 comprises a shooting unit 410, an exposure unit 420 and a controller 430. For example, the shooting unit 410 can be arranged on the collimator of the X-ray medical device 400 and the arrangement of the shooting unit is not limited to what is mentioned in the present disclosure; the controller 430 can be a controller contained in the detector of the X-ray medical device 400 or a controller independent of the detector, and the controller is not limited to what is mentioned in the present disclosure, either. The shooting unit (shooter) 410 can be a camera configured to acquire an image of the subject. In this example, a light and/or image may be projected onto the subject by a light source or projector. The exposure unit 420 may be radiation source, such as a radiation generator (radiator), x-ray tube, or tube head.

Wherein, the shooting unit 410 is configured to collect a visible light image of a subject under test, the exposure unit 420 is configured to pre-expose the subject under test with a set pre-exposure dose to obtain a first image, and the controller 430 is configured to: acquire a visible light image of the subject under test, define an initial ROI on the visible light image, define an ROI on the first image based on the initial ROI, define a reference pixel value based on the ROI, and calculate a main exposure dose for an actual exposure according to the reference pixel value. In an exemplary embodiment, the controller 430 includes processing circuitry that is configured to perform one or more functions/operations of the controller 430. Additionally, the shooter 410 and/or exposure unit 420 includes processing circuitry that is configured to perform one or more functions/operations of the respective components.

In the embodiments, the controller 430 is further configured to: display a preset selection box on the visible light image, and define at least one initial ROI by moving or adjusting the preset selection box on the visible light image.

For example, the preset selection box can be a preset selection box which is set in a preset position on the visible light image and has a preset size, or a preset selection box which is set in different positions according to the subject under test on the visible light image and has different sizes. In other words, for different subjects under test, a pre-estimated selection box located in different positions on the visible light image and having different sizes can be provided as a preset selection box. Alternatively, no preset selection box is provided and an initial ROI can be box-selected arbitrarily. In this case, the controller 430 is further configured to box-select an initial ROI on the visible light image. In practice, the operator can use an input device such as mouse to select and set an initial ROI, and the controller 430 performs the corresponding operation after receiving the corresponding input signal.

In the embodiments, the controller 430 is further configured to define an ROI by performing the following steps: defining the distance from the center of the initial ROI to the corresponding point of the center of the X-ray beam on the visible light image, and defining the position of the ROI on the first image according to the distance.

In addition, the present disclosure further provides a computer storage medium. Program instructions are stored in the computer storage medium, the program instructions can be run to realize the above-mentioned method, and the above-mentioned method can be applied to the medical device disclosed in the present disclosure. To be specific, a system or device equipped with a storage medium can be provided. Software program codes which can realize the function in any of the above-mentioned embodiments are stored in the storage medium, and the computer (or CPU or MPU) of the system or device can read and execute the program codes stored in the storage medium.

In this case, program codes read from the storage medium themselves can realize the function in any of the above-mentioned embodiments. Therefore, program codes and the storage medium where program codes are stored constitute a part of the present disclosure.

Embodiments of the storage medium used to provide program codes include a floppy disk, hard disk, magneto-optical disk, compact disc (for example, compact disk read-only memory (CD-ROM)), compact disk-recordable (CD-R), compact disk-rewritable (CD-RW), digital versatile disk-read only memory (DVD-ROM), digital versatile disk-random access memory (DVD-RAM), digital versatile disk+ rewritable (DVD+RW), magnetic tape, non-volatile memory card, and read-only memory (ROM). Alternatively, program codes can be downloaded from the server computer over a communication network.

In addition, it should clearly be understood that the function of any of the above-mentioned embodiments can be realized not only by executing the program codes read out by a computer, but also by letting the operating system running on the computer complete a part or all of practical operations through program code based instructions.

In addition, it should be understood that the program codes read out from a storage medium are written into the storage in the expansion board in a computer or are written into a storage in an expansion unit connected to the computer, and then the program code based instructions let the operation unit, such as a CPU, installed on the expansion board or expansion unit execute a part or all of practical operations to realize the function in any of the above-mentioned embodiments.

The present disclosure relates to an automatic exposure control method for X-ray imaging, a storage medium and a medical device. According to one embodiment, an automatic exposure control method for X-ray imaging comprises: acquiring a visible light image of a subject under test and defining an initial ROI on the visible light image. With the imaging quality guaranteed, the present disclosure can spare a physical automatic exposure control (AEC) chamber, and the number, positions and sizes of ROIs can be adjusted according to the actual requirements. The present disclosure is more flexible in patient positioning.

The above-mentioned embodiments are only preferred embodiments of the present disclosure, but are not used to restrict the present disclosure. Without departing the spirit and principle of the present disclosure, modifications, equivalent replacements, and improvements should all fall within the scope of protection of the present disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory.

REFERENCE LIST

100 Method
S110-S160 Steps
A Region
400 X-ray medical device
410 Shooting unit
420 Exposure unit
430 Controller

The invention claimed is:

1. An automatic exposure control method for X-ray imaging, comprising:
 acquiring a visible light image of a subject under test,
 defining an initial region-of-interest (ROI) on the visible light image,
 pre-exposing the subject under test with a set pre-exposure dose to obtain a first image,
 defining an ROI on the first image based on the initial ROI,
 defining a reference pixel value based on the ROI, and
 calculating a main exposure dose for an actual exposure according to the reference pixel value.

2. The automatic exposure control method for X-ray imaging as claimed in claim 1, wherein defining an initial ROI on the visible light image comprises:
 displaying a preset selection box on the visible light image, and
 defining the initial ROI by moving or adjusting the preset selection box on the visible light image.

3. The automatic exposure control method for X-ray imaging as claimed in claim 2, wherein:
 the preset selection box is a preset selection box having a preset size that is set in a preset position on the visible light image, or
 the preset selection box is a preset selection box having different sizes and that is set in different positions on the visible light image according to the subject under test displayed on the visible light image.

4. The automatic exposure control method for X-ray imaging as claimed in claim 1, wherein defining an initial ROI on the visible light image comprises: box-selecting an initial ROI on the visible light image.

5. The automatic exposure control method for X-ray imaging as claimed in claim 1, wherein defining an ROI on the first image comprises:
 defining a distance from a center of the initial ROI to a corresponding point of a center of an X-ray beam on the visible light image, and
 defining a position of the ROI on the first image according to the distance.

6. A non-transitory computer-readable storage medium, having program instructions stored thereon, that when executed, cause a processor to perform the method as claimed in claim 1.

7. The automatic exposure control method for X-ray imaging as claimed in claim 2, wherein defining an ROI on the first image comprises:
 defining a distance from a center of the initial ROI to a corresponding point of a center of an X-ray beam on the visible light image, and
 defining a position of the ROI on the first image according to the distance.

8. The automatic exposure control method for X-ray imaging as claimed in claim 3, wherein defining an ROI on the first image comprises:
 defining a distance from a center of the initial ROI to a corresponding point of a center of an X-ray beam on the visible light image, and defining a position of the ROI on the first image according to the distance.

9. The automatic exposure control method for X-ray imaging as claimed in claim 4, wherein defining an ROI on the first image comprises:
 defining a distance from a center of the initial ROI to a corresponding point of a center of an X-ray beam on the visible light image, and
 defining a position of the ROI on the first image according to the distance.

10. An X-ray medical device, comprising:
 a shooter configured to collect a visible light image of a subject under test,
 a radiator configured to pre-expose the subject under test with a set pre-exposure dose to obtain a first image, and
 a controller configured to:
  acquire a visible light image of the subject under test,
  define an initial region-of-interest (ROI) on the visible light image,
  define an ROI on the first image based on the initial ROI,
  define a reference pixel value based on the ROI, and
  calculate a main exposure dose for an actual exposure according to the reference pixel value.

11. The X-ray medical device as claimed in claim 10, wherein the controller is further configured to:
 display a preset selection box on the visible light image, and
 define the initial ROI by moving or adjusting the preset selection box on the visible light image.

12. The X-ray medical device as claimed in claim 11, wherein:
 the preset selection box is a preset selection box having a preset size and that is set in a preset position on the visible light image and has a preset size, or
 the preset selection box is a preset selection box having different sizes and that is set in different positions on the visible light image according to the subject under test displayed on the visible light image.

13. The X-ray medical device as claimed in claim 10, wherein the controller is further configured to: box-select an initial ROI on the visible light image.

14. The X-ray medical device as claimed in claim 10, wherein the controller is further configured to:
 defining the distance from the center of the initial ROI to the corresponding point of the center of an X-ray beam on the visible light image, and
 defining the position of the ROI on the first image, according to the distance, to define the ROI.

15. The X-ray medical device as claimed in claim 11, wherein the controller is further configured to:

defining the distance from the center of the initial ROI to the corresponding point of the center of an X-ray beam on the visible light image, and defining the position of the ROI on the first image, according to the distance, to define the ROI.

16. The X-ray medical device as claimed in claim 12, wherein the controller is further configured to:

defining the distance from the center of the initial ROI to the corresponding point of the center of an X-ray beam on the visible light image, and defining the position of the ROI on the first image, according to the distance, to define the ROI.

17. The X-ray medical device as claimed in claim 13, wherein the controller is further configured to:

defining the distance from the center of the initial ROI to the corresponding point of the center of an X-ray beam on the visible light image, and defining the position of the ROI on the first image, according to the distance, to define the ROI.

* * * * *